(12) United States Patent
Shimm

(10) Patent No.: US 6,887,255 B2
(45) Date of Patent: May 3, 2005

(54) LAPAROSCOPIC SPECIMEN EXTRACTION PORT

(76) Inventor: Peter Shimm, 4215 Thornapple St., Chevy Chase, MD (US) 20815

( * ) Notice: Subject to any disclaimer, the term of this patent is extended or adjusted under 35 U.S.C. 154(b) by 252 days.

(21) Appl. No.: 10/125,495

(22) Filed: Apr. 19, 2002

(65) Prior Publication Data

US 2003/0199915 A1 Oct. 23, 2003

(51) Int. Cl.$^7$ .............................................. A61M 29/00
(52) U.S. Cl. ........................ 606/191; 606/198; 606/200; 600/201; 600/204
(58) Field of Search ................................ 606/191, 194, 606/198, 200, 37, 108; 600/114, 201, 204, 210; 604/104–109

(56) References Cited

U.S. PATENT DOCUMENTS

| | | | | |
|---|---|---|---|---|
| 3,717,151 A | * | 2/1973 | Collett | ........................ 604/106 |
| 3,902,501 A | * | 9/1975 | Citron et al. | ................ 607/126 |
| 5,183,465 A | * | 2/1993 | Xanthakos et al. | ......... 604/108 |
| 5,263,937 A | * | 11/1993 | Shipp | ..................... 604/166.01 |
| 5,320,627 A | | 6/1994 | Sorensen et al. | |
| 5,370,647 A | | 12/1994 | Graber et al. | |
| 5,417,684 A | | 5/1995 | Jackson et al. | |
| 5,465,731 A | | 11/1995 | Bell et al. | |
| 5,577,993 A | * | 11/1996 | Zhu et al. | ..................... 600/204 |
| 5,591,177 A | | 1/1997 | Lehrer | |
| 5,643,313 A | | 7/1997 | Levin | |
| 5,707,359 A | | 1/1998 | Bufalini | |
| 5,788,709 A | | 8/1998 | Reik et al. | |
| 5,797,906 A | | 8/1998 | Rhum et al. | |
| 5,971,960 A | * | 10/1999 | Flom et al. | ................. 604/174 |
| 5,980,544 A | | 11/1999 | Vaitekunas | |
| 6,059,734 A | | 5/2000 | Yoon | |
| 6,074,408 A | | 6/2000 | Freeman | |
| 6,152,932 A | | 11/2000 | Ternström | |
| 6,203,517 B1 | | 3/2001 | Shipp et al. | |
| 6,206,889 B1 | | 3/2001 | Bennardo | |
| 6,508,825 B1 | * | 1/2003 | Selmon et al. | .............. 606/198 |

* cited by examiner

Primary Examiner—Anhtuan T. Nguyen
Assistant Examiner—Tan-Uyen T. Ho
(74) Attorney, Agent, or Firm—Pillsbury Winthrop LLP

(57) ABSTRACT

A laparoscopic surgical extraction port (LSEP) includes a port having a radially-enlarged distal end. A sheath having a plurality of circumferentially-spaced prongs is slidingly mounted onto the port. With the prongs contracted radially-inwardly and the LSEP in its contracted position, a surgeon inserts the LSEP into a patient's abdominal cavity through an incision. The surgeon then expands the LSEP by pulling the port rearwardly such that the radially-enlarged distal end expands the prongs radially-outwardly. The surgeon then positions a specimen and endo-bag in the funnel formed by the expanded prongs. The specimen, endo-bag, and prongs are thereafter simultaneously extracted through the incision. A radially-inward force that is applied to the prongs by the incision substantially prevents the specimen from bunching or rupturing during the extraction process.

20 Claims, 14 Drawing Sheets

LAPAROSCOPIC SPECIMEN EXTRACTION PORT

BACKGROUND OF THE INVENTION

1. Field of the Invention

The present invention relates generally to laparoscopic trocars/ports, and more specifically to laparoscopic specimen extraction ports (LSEPs) that prevent the extracted specimen from bunching up in an endoscopic specimen retrieval bag prior to removal through the abdominal wall, for example.

2. Description of Related Art

As illustrated in FIG. 11, during a typical abdominal laparoscopic surgery, a surgeon makes four or so small (typically about 2 cm) incisions 10 in the abdominal wall 20 of the patient. The surgeon positions a trocar 22 (shown in FIGS. 15 and 16) into an axial hole 26 in a laparoscopic port 30 to facilitate insertion of the port 30 into the incision 10. After inserting the trocar 22 and port 30 through the incision 10, the surgeon removes the trocar 22 to allow insertion of surgical instruments (e.g., grasping instrument 80) into the abdominal cavity 40 through the axial hole 26 in the port 30. The surgeon repeats this procedure for each of the four or so required ports 30.

To simplify the figures and focus on the functional structures of the laparoscopic port 30 and trocar 22, FIGS. 11–14 illustrate simplified views of the conventional laparoscopic port 30. It is to be understood, however, that in reality, conventional laparoscopic ports 30 and trocars 22 are typically shaped as shown in FIGS. 15 and 16. Similar types of simplified views are used to illustrate the present invention. Nonetheless, as would be appreciated by one of ordinary skill in the art, the present invention will, in practice, have a shape similar to the laparoscopic port 30 and trocar 22 illustrated in FIGS. 15 and 16.

The surgical instruments that are inserted through the laparoscopic port 30 typically include a video camera that enables the surgeon to visualize the surgical procedure. Variously sized surgical ports 30 are designed to be used with variously sized instruments. Typical instruments require surgical ports 30 with axial holes 26 having 5 mm inside diameters. As is discussed in greater detail below, endoscopic specimen retrieval bags ("endo-bags™") typically are inserted through ports 30 that have holes 26 with 10 mm inside diameters and 12 mm outside diameters.

During laparoscopic surgery, the abdomen is insufflated with carbon dioxide to distend the abdominal cavity 40 (creating pneumoperitoneum) and allow for better visualization of the surgical operation. Each port 30 includes a flapper valve 45 (see FIGS. 15 and 16) that opens to allow the surgeon to insert an instrument therethrough and automatically closes when the instrument is removed so as to prevent the loss of pneumoperitoneum.

During laparoscopic surgery, it is often necessary to extract a specimen 50 such as a gall bladder from the abdominal cavity 40 of the patient. As illustrated sequentially in FIGS. 11–14, using a convention specimen extraction technique, the surgeon inserts an endo-bag 60 through one of the ports 30 and positions the endo-bag 60 using an endo-bag handle/controller 70. As illustrated in FIG. 11, after the specimen 50 has been surgically detached from the patient, the surgeon uses a surgical grasping instrument 80, which is inserted into the abdominal cavity 40 through a separate port 30, to place the specimen into the open endo-bag 60. As illustrated in FIG. 12, the surgeon pulls a "purse string" 90 of the endo-bag 60 to synch down the open end of the endo-bag 60, thereby securely enclosing the specimen 50 within the endo-bag 60. As illustrated in FIG. 13, the surgeon then removes the port 30 through which the endo-bag 60 was inserted, leaving the purse string 90 extending through the incision 10. This unfortunately often causes loss of pneumoperitoneum, leading to impaired visualization of the specimen 50 extraction process. The surgeon thereafter attempts to pull the endo-bag 60 and specimen 50 out of the abdominal cavity 40 through the incision 10.

Unfortunately, as illustrated in FIG. 14, it is frequently difficult for the surgeon to extract the specimen 50 and endo-bag 60 through the relatively small incision 10. As the surgeon pulls the endo-bag 60 through the incision 10, most of the plastic endo-bag 60 easily pulls through the incision 10 with the specimen 50 bunching in the bottom of the endo-bag 60 in the abdominal cavity 40 (as shown in FIG. 14). Such bunching results in a variety of deleterious effects. In one example, the surgeon may resort to exerting a strong pulling force on the endo-bag 60, causing the endo-bag 60 and/or the surgical specimen 50 to rupture. Such a rupture might spread infectious, bilious, and/or even cancerous material in the abdominal wall 20 and cavity 40. Alternatively, the surgeon may resort to extending his/her initially relatively small port incision 10. Expanding the incision 10 deleteriously increases postoperative pain, increases surgical blood loss, increases the risk of future dehiscence (opening) of the incision and/or herniation of the abdominal contents through the expanded incision 10, and reduces or eliminates the advantages of laparoscopic surgery. Furthermore, the complications that often accompany the specimen 50 extraction procedure add significant operating room and anesthetic time to the surgery, which greatly increases the cost of the procedure to the hospital and the patient.

In summary, while prior art laparoscopic ports 30 and procedures(s) (as outlined above in connection with FIGS. 11–14) have proven effective, for the most part, in laparoscopic surgery, the prior art ports 30 available (and, therefore, the procedure(s) used in connection with those ports 30) may lead unnecessarily to complications. This has resulted in a need for an improved port and/or procedure to lessen the occurrence of such complications.

SUMMARY OF THE INVENTION

One aspect of the present invention, therefore, provides an improved laparoscopic trocar/port that reduces surgery time and post-operative recovery time.

An additional aspect of the present invention provides a laparoscopic trocar/port that substantially prevents a specimen from bunching in an endo-bag during extraction of the specimen from a patient.

A further aspect of the present invention provides a laparoscopic trocar/port that reduces the risk of rupturing the specimen or endo-bag during extraction of the specimen from a patient.

A further aspect of the present invention provides a laparoscopic trocar/port that reduces the risk of spreading infectious, bilious, and/or cancerous material into the patient's abdominal cavity and/or incision.

A further aspect of the present invention provides a laparoscopic specimen extraction port (LSEP) having expanded and contracted positions. The laparoscopic specimen extraction port has an elongated, hollow port with a rearward portion, an intermediate portion, and a forward portion that is radially-enlarged relative to the intermediate portion. A holding ring is disposed radially-outwardly from the intermediate portion and adapted to slide relative to the intermediate portion. The holding ring is disposed at a rear end of the intermediate portion when the laparoscopic specimen extraction port is in the contracted position. A plurality of circumferentially-spaced prongs have rearward ends connected to the holding ring and forward ends extending to the radially-enlarged, forward portion. The forward ends of the prongs expand radially-outwardly relative to the rearward ends when the laparoscopic specimen extraction port is in the expanded position. During the transition from the contracted to the expanded position, the radially-enlarged forward portion expands the prongs radially-outwardly.

According to a further aspect of the present invention, the laparoscopic specimen extraction port has a releasable holding mechanism to selectively secure the holding ring at the rear end of the intermediate portion when the laparoscopic specimen extraction port is in the contracted position.

According to a further aspect of the present invention, an indentation is formed on a surface of the holding ring to define a folding line between the holding ring and the prongs.

Additional and/or alternative objects, features, aspects, and advantages of the present invention will become apparent from the following description, the accompanying drawings, and the appended claims.

BRIEF DESCRIPTION OF THE DRAWINGS

For a better understanding of the present invention as well as other objects and further features thereof, reference is made to the following description which is to be used in conjunction with the accompanying drawings, where.

DETAILED DESCRIPTION OF PREFERRED EMBODIMENTS OF THE INVENTION

Figure 1:
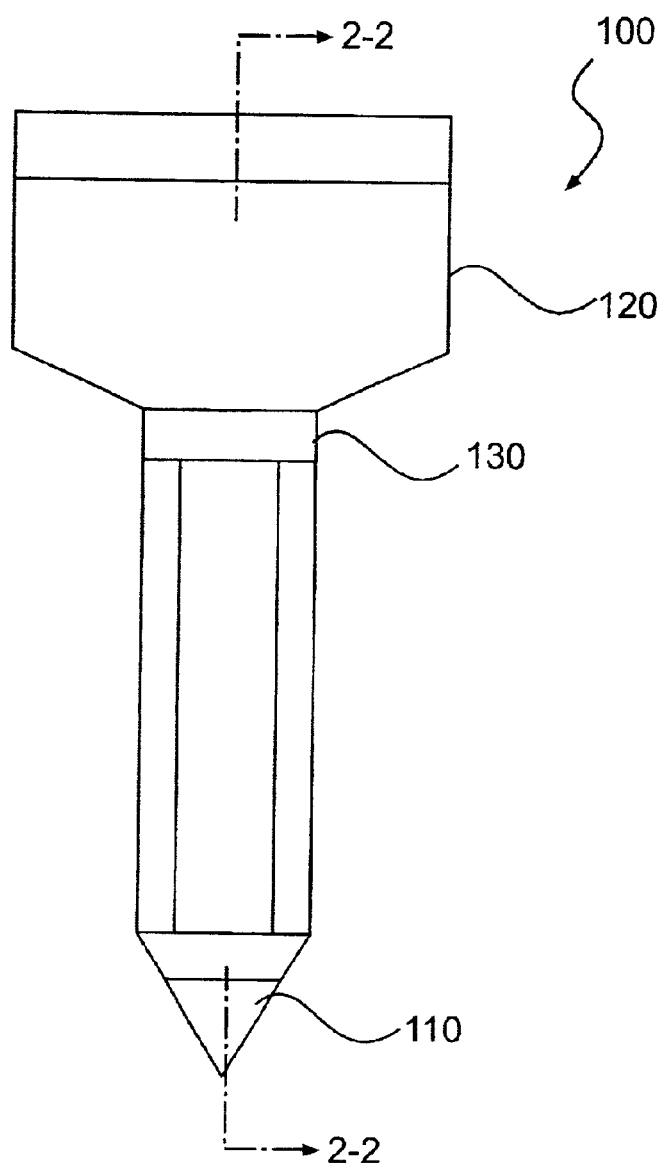
FIG. 1 is a side view of an LSEP according to the present invention.

FIG. 1 is a side view of an LSEP 100 according to the present invention. The LSEP 100 includes a pointed trocar 110, a port 120, and a sheath 130. The LSEP 100 has expanded and contracted positions.

Figure 2:
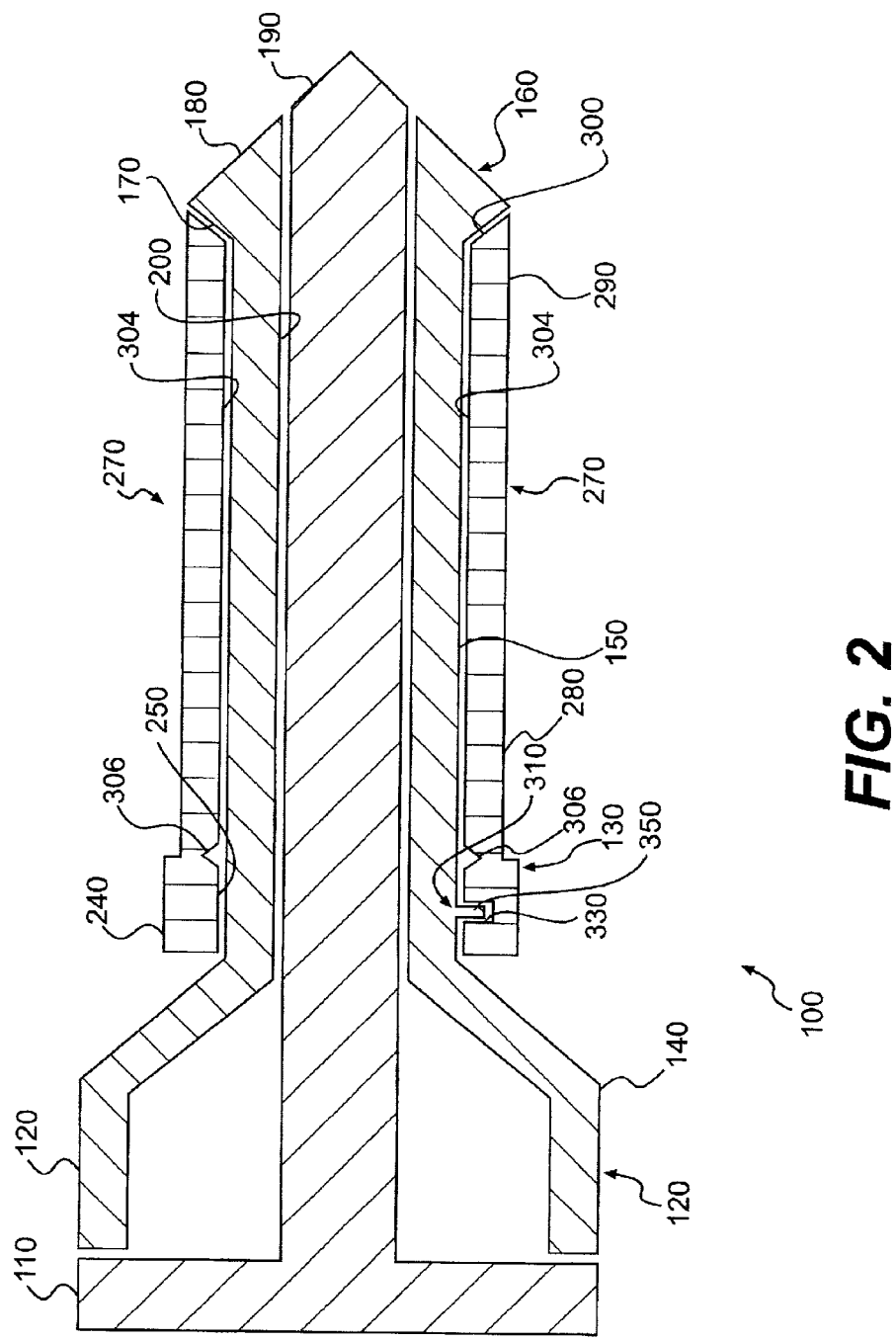
FIG. 2 is a cross-section of the LSEP illustrated in FIG. 1, taken along the line 2—2 in FIG. 1.
Figure 3:
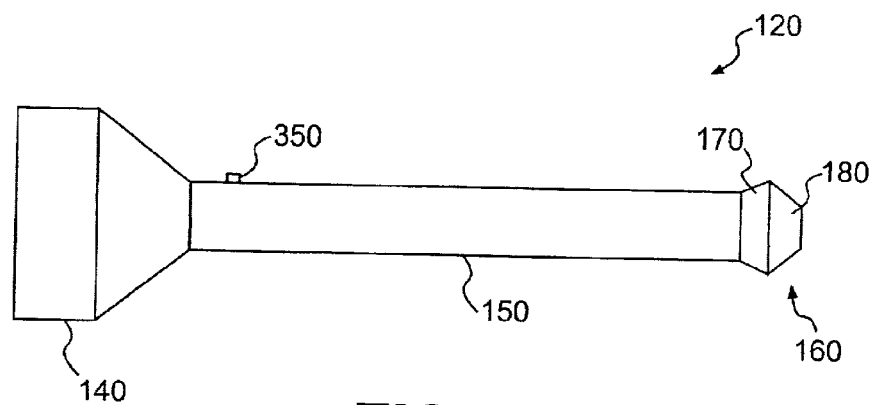
FIG. 3 is a side view of a port of the LSEP of FIG. 1.
Figure 15:
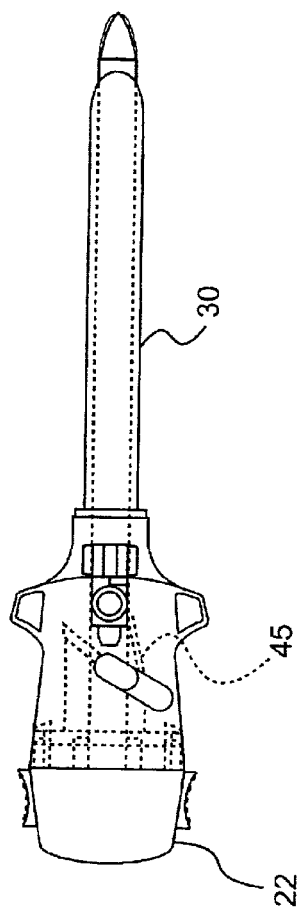
FIGS. 15 and 16 are side views showing an interaction between a conventional trocar and LSEP.
Figure 16:
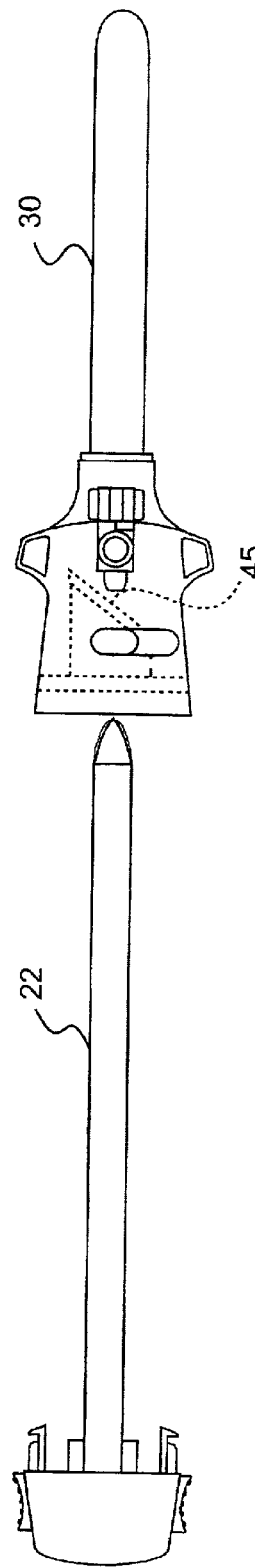

As illustrated in FIGS. 2 and 3, the port 120 is elongated and hollow. A rearward (or proximal) portion 140 of the port 120 is generally funnel-shaped and tapers radially-inwardly toward an intermediate portion 150. A flapper valve (not shown) like the conventional flapper valve 45 illustrated in FIGS. 15 and 16 is preferably disposed in the rearward portion 140 to preserve pneumoperitoneum during surgery when surgical instruments are not inserted through the port 120. The intermediate portion 150 is longitudinally elongated and preferably has a constant cross-section over its longitudinal length. As would be appreciated by one of ordinary skill in the art, however, the intermediate portion 150 need not have a constant cross-section over its longitudinal length. To the contrary, the cross-section may be tapered inwardly or outwardly along its length. In addition, the cross-section may vary over its longitudinal length. As would be appreciated by those of ordinary skill in the art, the precise configuration of the cross-section of the intermediate portion 150 is not critical to the operation of the present invention.

As illustrated in FIG. 3, a forward (or distal) portion 160 of the port 120 extends forwardly from the intermediate portion 150 and is radially-enlarged relative to the intermediate portion 150. The forward portion 160 includes an outer surface 170 that tapers radially-outwardly from a forward end of the intermediate portion 150. The outer surface 170 is preferably frustroconical but may alternatively form other shapes. The forward portion 160 also includes a forward tip 180 that tapers radially-inwardly from the forward edge of the outer surface 170. The inward taper of the forward tip 180 preferably matches an inward taper of an inwardly-tapering tip 190 of the trocar 110 such that when the trocar 110 is inserted into the port 120 (as shown in FIGS. 1 and 2), the tip 190 of the trocar 110 and the forward tip 180 of the port 120 combine to form a pointed forward tip that is adapted to be inserted through the incision 10 of the patient.

As illustrated in FIG. 2, the intermediate and forward portions 150, 160 include a longitudinally-extending bore 200 therethrough. The bore 200 has a diameter that is sufficiently large to allow insertion of an endo-bag or other surgical instruments therethrough. The bore 200 is preferably between 10 and 14 mm in diameter. An outside diameter of the main portion of the trocar 110 is slightly smaller than the diameter of the bore 200 so that the trocar 110 can be inserted into the port 120.

The overall longitudinal length of the port 120 is preferably about the same as conventional laparoscopic ports/trocars so that conventional surgical instruments can be used with the LSEP 100.

The port 120 may comprise a variety of materials. A disposable port 120 may comprise plastic or PVC. Conversely, a reusable port 120 may comprise steel.

Figure 4:
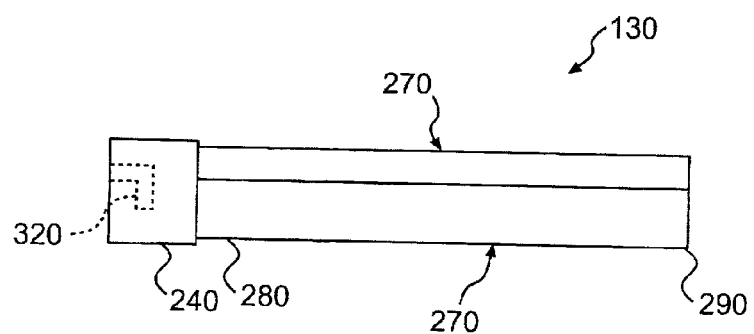
FIG. 4 is a side view of a sheath of the LSEP of FIG. 1.

As illustrated in FIGS. 2 and 4, the sheath 130 includes a holding ring 240 that is manufactured as an integral part of the intermediate portion 150 to allow the holding ring 240 to slide longitudinally (forwardly and rearwardly) on the intermediate portion 150. An inner surface 250 of the holding ring 240 has an inner diameter that is smaller than the largest diameter of the outer surface 170 of the forward portion 160. Consequently, the holding ring cannot slide forwardly relative to the port 120 past the forward portion 160. Similarly, the inner diameter of the holding ring 240 is smaller than the funnel shape of the rearward portion 140 so that the holding ring 240 cannot slide rearwardly past the rearward portion 140. When the LSEP 100 is in the contracted position, the holding ring 240 is longitudinally disposed at a rearward end of the intermediate portion 150.

While the holding ring 240 is shown as an integral portion of the sheath 130, it should be noted that the holding ring 240 may be manufactured as a separate component that is connected to the sheath 130. In such a case, the holding ring 240 may be connected to the sheath 130 in any suitable fashion. For example, the holding ring 240 may be welded, glued, bolted, threadedly affixed, etc. to the sheath 130 without departing from the scope of the present invention.

The sheath 130 includes a plurality of circumferentially-spaced prongs 270 having rearward ends 280 connected to the holding ring 240. As illustrated in FIG. 2, forward ends 290 of the prongs 270 extend forwardly toward the forward portion 160. The forward ends 290 include forward tips having inside surfaces 300 that taper radially-outwardly as they extend forwardly. Consequently, the inside surfaces 300 of the forward tips of the prongs 270 adjoin the outwardly-tapering outer surface 170 of the forward portion 160 when the LSEP 100 is in the contracted position.

In the illustrated embodiment, three circumferentially-spaced prongs 270 each cover an annular arc of about 120 degrees. It should be noted, however, that the sheath 130 may include a greater or fewer number of prongs 270 without deviating from the scope of the present invention. When the LSEP 100 is in the contracted position, inner surfaces 304 of the prongs 270 generally form a bore that has a diameter that is slightly larger than an outer diameter of the intermediate portion 150. The diameter of the bore is preferably equal to the inside diameter of the holding ring 240 so that the holding ring 240 and prongs 270 form a generally smooth inside bore when in the contracted position.

The inner surfaces 304 of the prongs 270 are smooth so that they do not abrade an endo-bag. Alternatively, the inner surfaces 304 may be textured to help grab an endo-bag as the LSEP 100 extracts a specimen. Alternatively, the inner surface 304 may have a longitudinal ridge or rail that rides in a groove on the outer surface of the intermediate portion 150 of the port 120. The outer surfaces of the prongs 270 are also smooth so that the sheath 130 can more easily slide in and out of an incision 10. The edges of the prongs 270 are preferably at least slightly curved and smoothed so that they do not include any sharp edges that might cut into the patient during surgery.

In the illustrated embodiment, the holding ring 240 and prongs 270 are integrally formed. However, the prongs 270 may alternatively be connected to the holding ring 240 after formation.

As shown in FIG. 2, the holding ring 240 preferably includes an annular indentation 306 at or near the transition between the inner surface 250 of the holding ring 240 and the inner surface 304 of the prongs 270. The annular indentation 306 marks the transition from the holding ring 240 to the prongs 270. The annular indentation 306 facilitates the outward radial movement of the prongs 270 away from the intermediate portion 150 when the LSEP 100 is manipulated into the expanded position. While the annular indentation 306 is shown with a V-shaped cross-section, any other suitable cross-section may be used without deviating from the scope of the present invention. For example, the annular indentation 306 may have a U-shape or a rectangular shape. Regardless of the actual shape employed, the function of the indentation is to facilitate the outward radial expansion of the prongs 270 by providing a folding line.

As would be appreciated by one of ordinary skill in the art, the annular indentation 306 need not be annular to function as a folding line. In an alternate construction, the indentation 306 may comprise a series of indentations that extend around the inner surface 250 of the holding ring 240 and sheath 130. Still further, the indentation 306 may comprise two or more parallel indentations on the inner surface 250 of the holding ring 240 and the sheath 130. Still further, the indentation 306 may be formed on an outside surface of the holding ring 240. In yet another embodiment, where the prongs 270 are sufficiently flexible (either because of the material used or the thickness of the material used), no indentation 306 may be included.

As illustrated in FIG. 2, the holding ring 240 and prongs 270 comprise a strong, flexible material such as plastic or PVC. Consequently, when the LSEP 100 is transitioned from the contracted position into the expanded position, as is discussed in greater detail below, the prongs 270 flex such that the forward ends 290 expand radially-outwardly relative to the rearward ends 280 to form a funnel shape that includes a wedge-shaped gap formed between adjoining prongs 270. Alternatively, the prongs 270 may comprise a stronger, more rigid material such as steel and be hinged at their rearward ends 280 to the holding ring 240, which may also comprise a rigid material such as steel, such that the prongs 270 pivot radially-outwardly when the LSEP 100 is moved into the expanded position. While the material composition of the prongs 270 will dictate the design of their radial thickness so that the prongs 270 flex appropriately during expansion of the LSEP 207, as would be appreciated by one of ordinary skill in the art, the radial thickness of the prongs 270 is preferably about 1 or 2 mm.

As an illustrative example, if the port 120 has a 12 mm inside diameter and has a radial thickness of 1 mm and the prongs 270 have a 2 mm radial thickness and flushly adjoin the intermediate portion 150 of the port 120 when in the contracted position, an overall outside diameter of an intermediate portion of the LSEP 100 would be 18 mm.

In the illustrated embodiment, the prongs 270 touch each other when the LSEP 100 is in the contracted position (see FIG. 4). However, the widths of the prongs 270 may be reduced such that, even in the contracted position, there is an longitudinally-extending circumferential gap between adjoining prongs 270. Conversely, the widths of the prongs 270 may also be widened such that adjoining prongs 270 overlap each other like the petals of a rose such that, even when the LSEP 100 is in the expanded position, adjoining prongs 270 touch each other and form a full funnel shape without gaps.

If the prongs 270 touch each other when the LSEP 100 is in the contracted position (see FIG. 4), the prongs 270 could be attached to each other by a substance that, if broken off inside the abdominal cavity 40, is absorbed by the patient's body. A derivative of lactic acid may be one such material, since it is readily absorbed by the body. As would be appreciated by those skilled in the art, however, derivatives of lactic acid are not the only substance that may be employed for this purpose. To the contrary, those of ordinary skill in the art would readily recognize that there are a plethora of materials that are absorbable by the body that may be used for this purpose.

The prongs 270 are preferably tinted with a color that is not normally present in the abdominal cavity 40 of a patient. Possible colors include orange, bright green, etc. Such coloring aids the surgeon in seeing the prongs 270. Additionally, the inside surfaces 304 and outside surfaces of the prongs 270 may be colored differently to help the surgeon know what side of each prong 270 he/she is looking at. If the prongs 270 are colored to be distinguishable from tissue, the prongs 270 are also easily identifiable if one or more of the prongs 270 should accidentally separate from the holding ring 240 during surgery. This greatly facilitates identification and removal from the patient. Alternatively, the prongs 270 may be made from (or incorporate) a radio-opaque material. If made from a radio-opaque material (or if incorporating a radio-opaque material at least in part therein), the prongs 270 may be easily located by illumination with x-ray. Therefore, if one of the prongs 270 should be disengaged from the holding ring 240, it may be more easily located.

Figure 5:
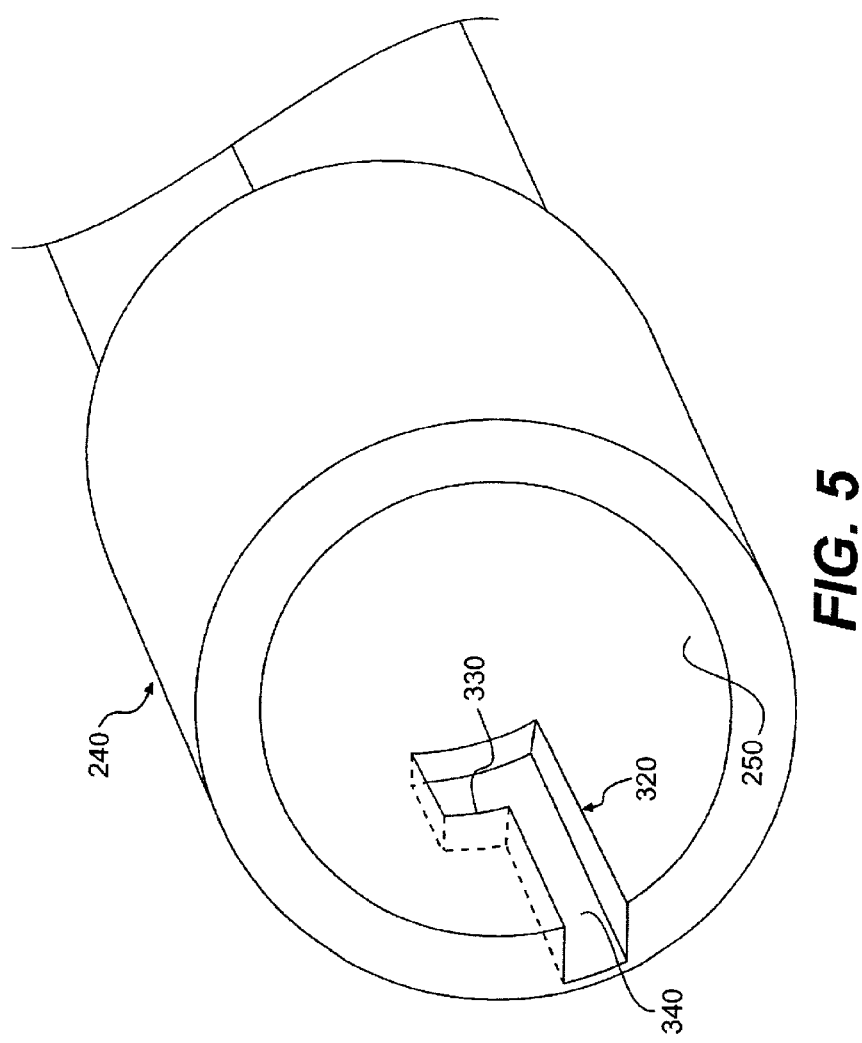
FIG. 5 is a partial perspective view of the sheath of the LSEP of FIG. 1, as viewed from the rearward side of the sheath.

As illustrated in FIG. 2, a releasable holding mechanism 310 selectively secures the holding ring 240 at the rear end of the intermediate portion 150 when the LSEP 100 is in the contracted position. As illustrated in FIGS. 4 and 5, the holding mechanism 310 includes an L-shaped groove 320 on the inner surface 250 of the holding ring 240. A forwardly-facing surface 330 is defined on one circumferentially-extending leg of the groove 320. The other leg of the groove 320 extends rearwardly from the first leg to the rearward end of the holding ring 240 and defines a rearwardly-extending notch 340. As illustrated in FIGS. 2 and 3, the holding mechanism 310 also includes a protrusion 350 extending radially-outwardly from the outer surface of a rearward portion of the intermediate portion 150. As illustrated in FIG. 2, when the LSEP 100 is in the contracted position, a rearward edge of the protrusion 350 is positioned in front of the forwardly-facing surface 330. Consequently, the holding mechanism 310 prevents the holding ring 240 from sliding forwardly relative to the port 120 when the LSEP is in the contracted position. To extend the LSEP 100 into the expanded position, the surgeon rotates the port 120 (counterclockwise as viewed from the rear end of the LSEP 100 in the illustrated embodiment) relative to the holding ring 240 until the protrusion 350 aligns with the notch 340. The protrusion 350 can thereafter move through the notch 340 and the port 120 can move rearwardly relative to the holding ring 240 to permit the surgeon to manipulate the LSEP 100 into the expanded position.

While only one is illustrated in FIGS. 4 and 5, the holding mechanism 310 may include a plurality of mating sets of protrusions 350 and L-shaped grooves 320, as would be appreciated by one of ordinary skill in the art.

The holding mechanism 310 may also include a safety device that tends to prevent the holding mechanism 310 from accidentally releasing. Such a safety device may function in the same manner as safety caps for medicine bottles. Alternatively, the safety device may include a break-away ring like the rings used on milk jugs to prevent the port 120 from rotating relative to the holding ring 340 until a sufficient torque is supplied.

While in the illustrated embodiment, the holding mechanism 310 comprises a protrusion 350 and mating groove 340, the holding mechanism 310 may comprise a variety of other types of mechanisms without deviating from the scope of the present invention. For example, the holding mechanism 310 may alternatively comprise a threaded portion on the holding ring 240 and a mating threaded portion on the intermediate portion 150 such that the surgeon releases the holding mechanism 310 by unscrewing the port 120 from the holding ring 240.

In the illustrated embodiment, the cross-sections of the port 120 and sheath 130 are circular. However, the present invention is not so limited. Other cross-sections such as ovoid shapes may also be used. Nonetheless, circular cross-sections are preferred because they include smooth curves and provide the largest cross-sectional area for the bore 200 relative to an outer perimeter (and therefore incision 10 size) of the sheath 130. In addition, a circular cross-section facilitates rotational movement of the sheath 130 relative to the port 120

The operation of the LSEP 100 is described with sequential reference to FIGS. 610. To use the LSEP 100, the surgeon first inserts the contracted LSEP 100 and trocar 110 into an incision 10 in the abdominal wall 20 of the patient. The surgeon then removes the trocar 110 and can use the port 120 with conventional surgical instruments. During such use, the sheath 130 is disposed between the port 120 and the incision 10.

Figure 6:
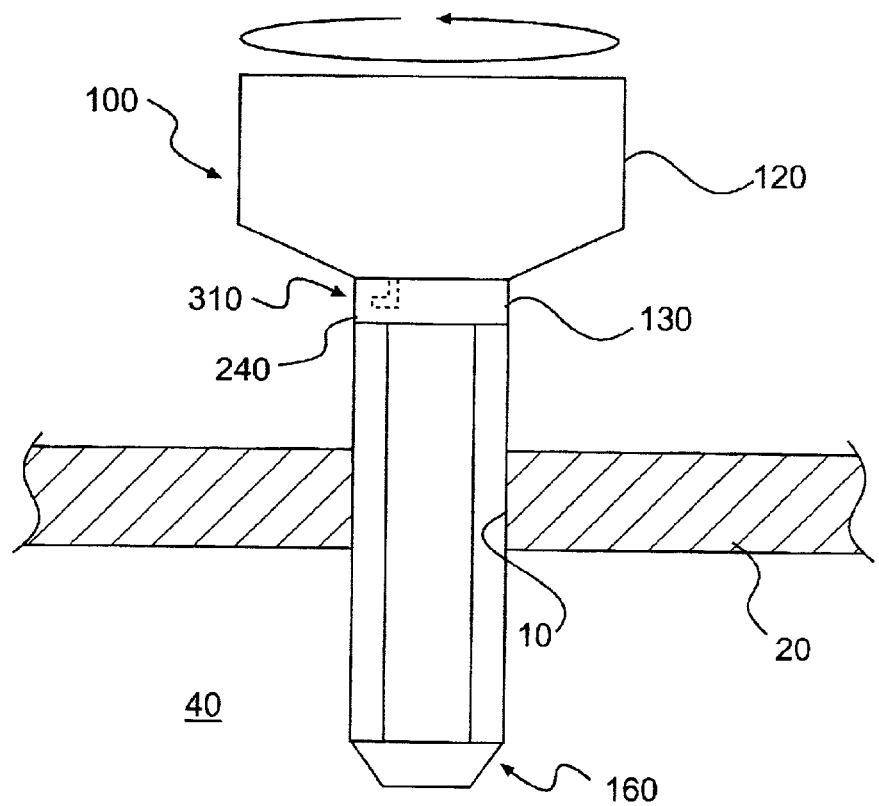
FIGS. 6–10 are side views showing the sequential operation of the LSEP of FIG. 1.

As illustrated in FIG. 6, when the surgeon uses the LSEP 100 to extract a specimen 50, the surgeon first rotates the port 120 relative to the sheath 130 to release the holding mechanism 310.

Figure 7:
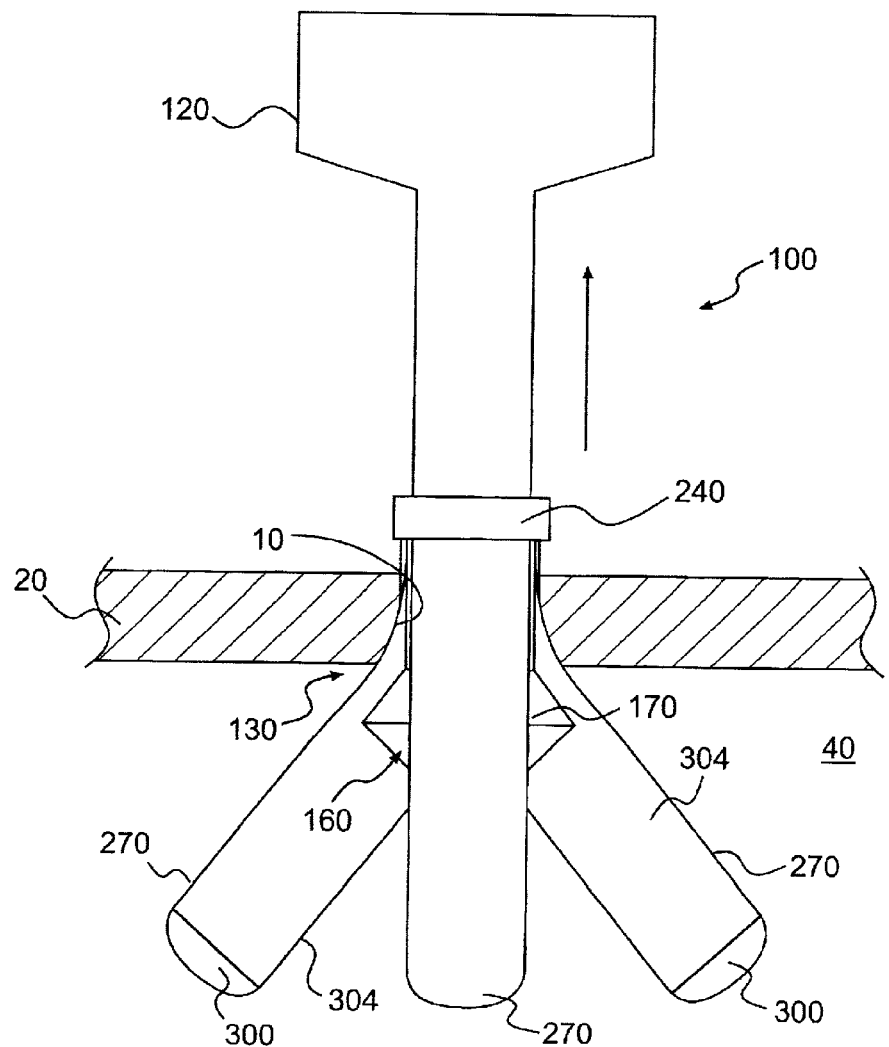
Figure 8:
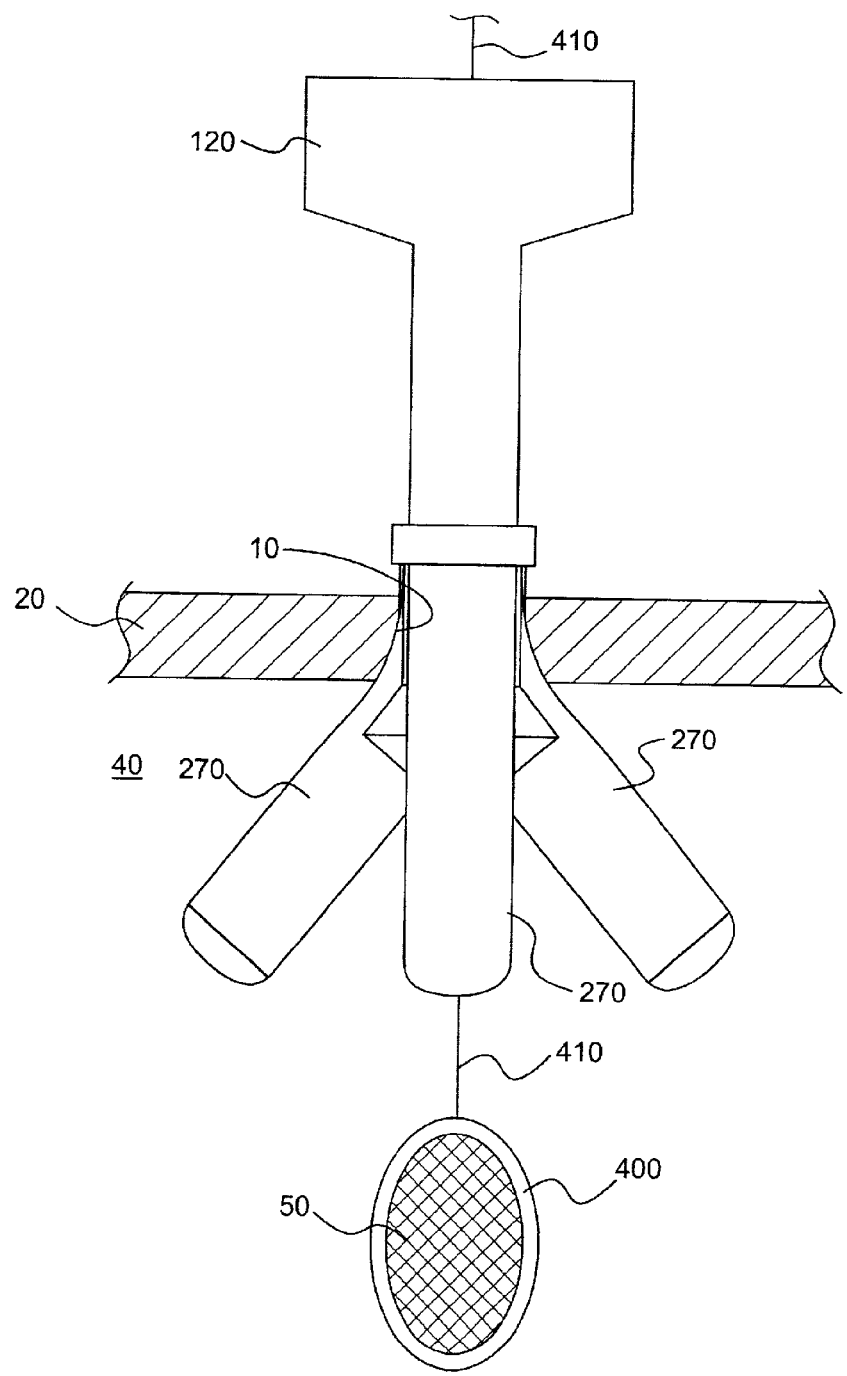

As illustrated in FIG. 7, the surgeon next uses one of his/her hands to hold the holding ring 240 stationary relative to the patient and uses his/her other hand to slide the port 120 rearwardly (in the direction of the arrow) relative to the holding ring 240. As the forward portion 160 slides rearwardly relative to the prongs 270, the tapered outer surface 170 of the forward portion slidingly engages the inside surfaces 300 of the forward ends 290 of the prongs 270, thereby forcing the forward ends of the prongs 270 to flex radially-outwardly. Thereafter, the outer surface 170 of the forward portion 160 of the port 120 engages inner surfaces 304 of the prongs 270, further expanding the prongs 270 as the LSEP 100 transitions into increasingly expanded positions. When the forward portion 160 approaches the holding ring 240, the port 120 cannot slide further rearwardly relative to the holding ring 240 because the inside diameter of the holding ring 240 and the rearward ends 280 of the prongs 270 are smaller than the outer diameter of the forward portion 160. FIG. 8 illustrates the fully expanded position of the LSEP 100.

As illustrated in FIG. 8, the surgeon then inserts an endo-bag 400 into the abdominal cavity 40 through the port 120. It should be noted that the endo-bag 400 is usually inserted into the abdominal cavity 40 before the LSEP 100 is manipulated into the expanded position. The surgeon then places the specimen 50 into the endo-bag 400 using a conventional technique.

Like the endo-bag 60, the endo-bag 400 includes a purse string 410 closing mechanism. It is believed that the endo-bag 400 to be used with the LSEP 100 will have to be longer than endo-bags 60 used in the prior art. In prior art endo-bags 60, the surgeon often pulled a portion of the endo-bag 60 out from the top of the port 30 prior to extraction of the port 30 and endo-bag 60 from the patient. The surgeon typically would grasp the top of the endo-bag 60 during removal of the specimen 50 from the patient. To provide the same operation with the LSEP 100, the endo-bag 400 will probably be longer than the conventional endo-bag 60 because it will have to extend through both the port 120 and sheath 130 when in the expanded position.

Figure 9:
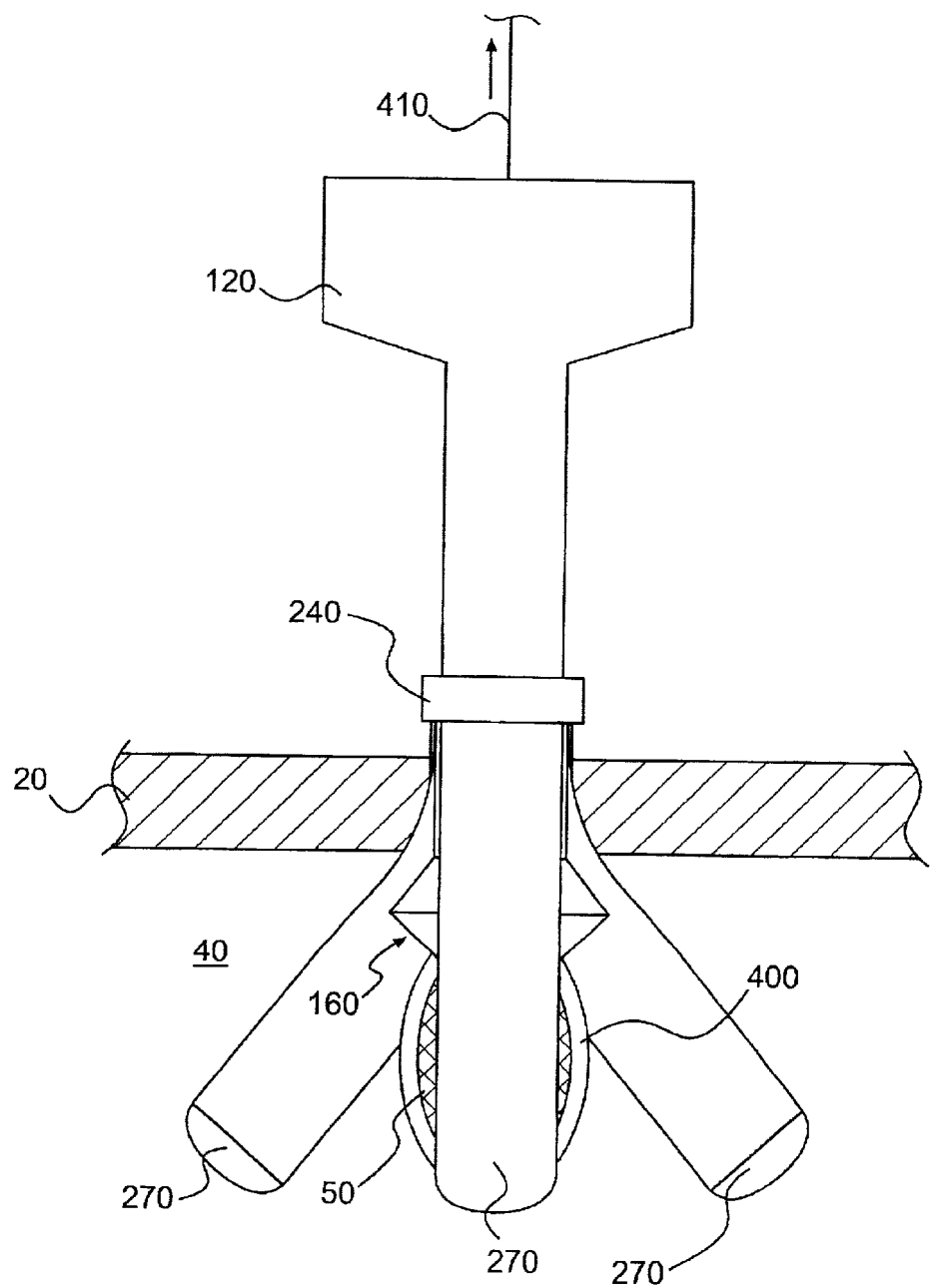

As illustrated in FIG. 9, after placing the specimen 50 into the endo-bag 400, the surgeon pulls the purse string 410 in the direction of the arrow at the rearward end of the port 120. Pulling the purse string 410 closes the endo-bag 400 and moves the endo-bag 400 and specimen 50 toward and into the funnel shape formed by the expanded prongs 270 of the LSEP 100 in the expanded position.

Figure 10:
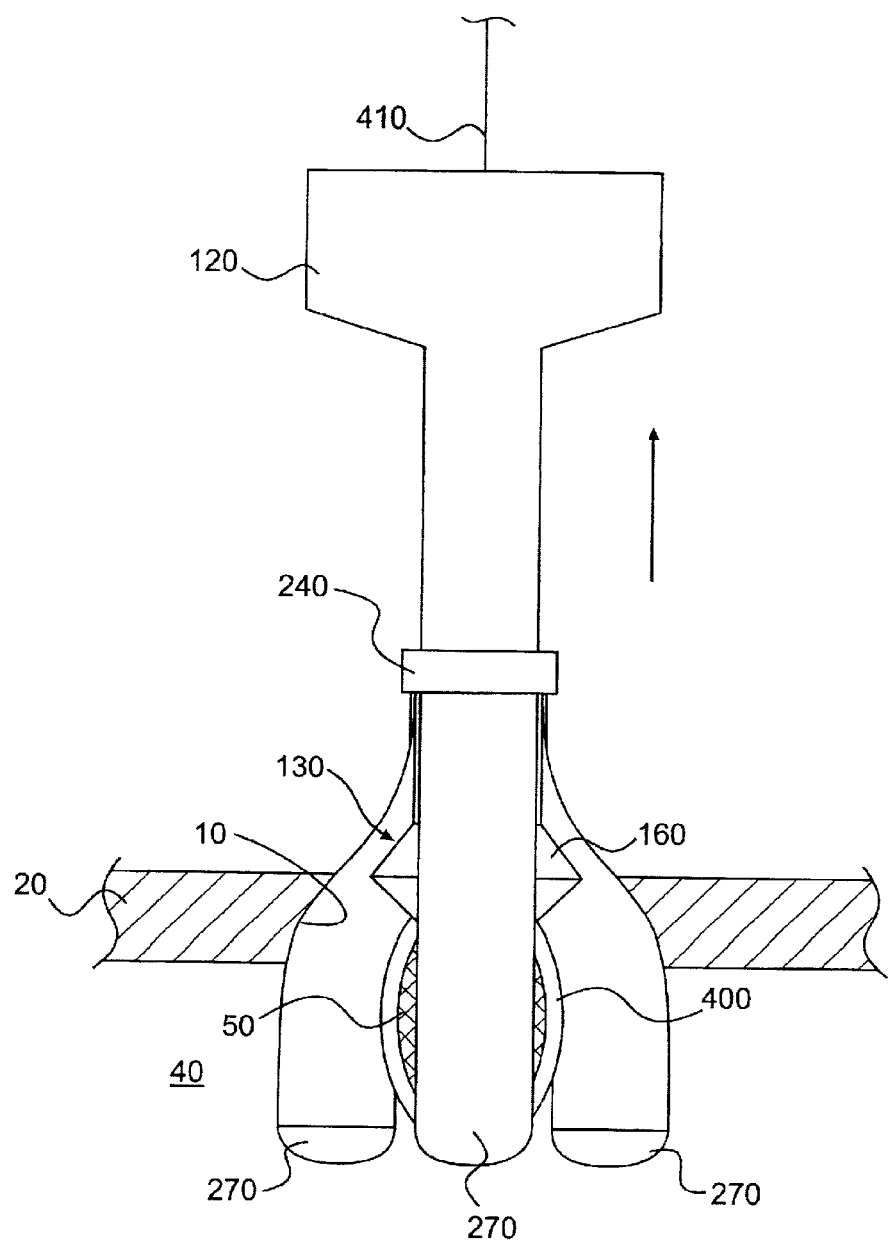
Figure 11:
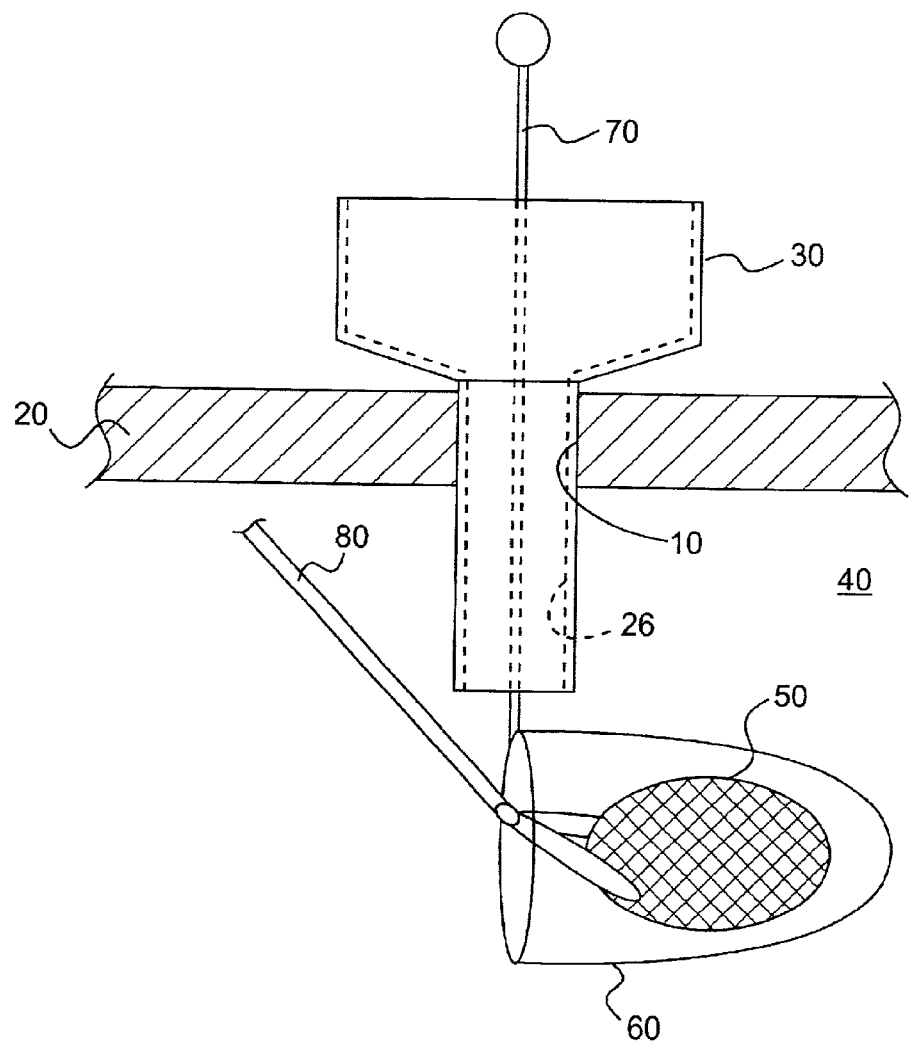
FIGS. 11–14 are side views showing the sequential operation of a conventional LSEP.
Figure 12:
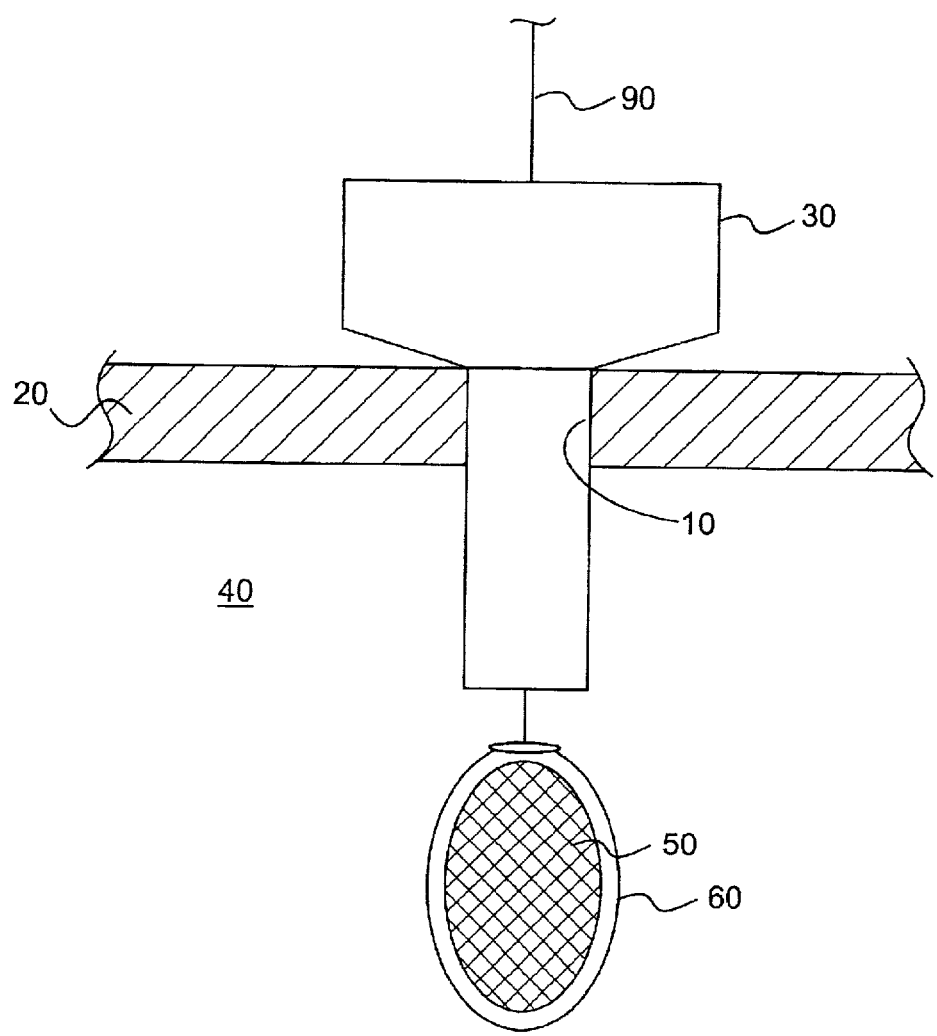
Figure 13:
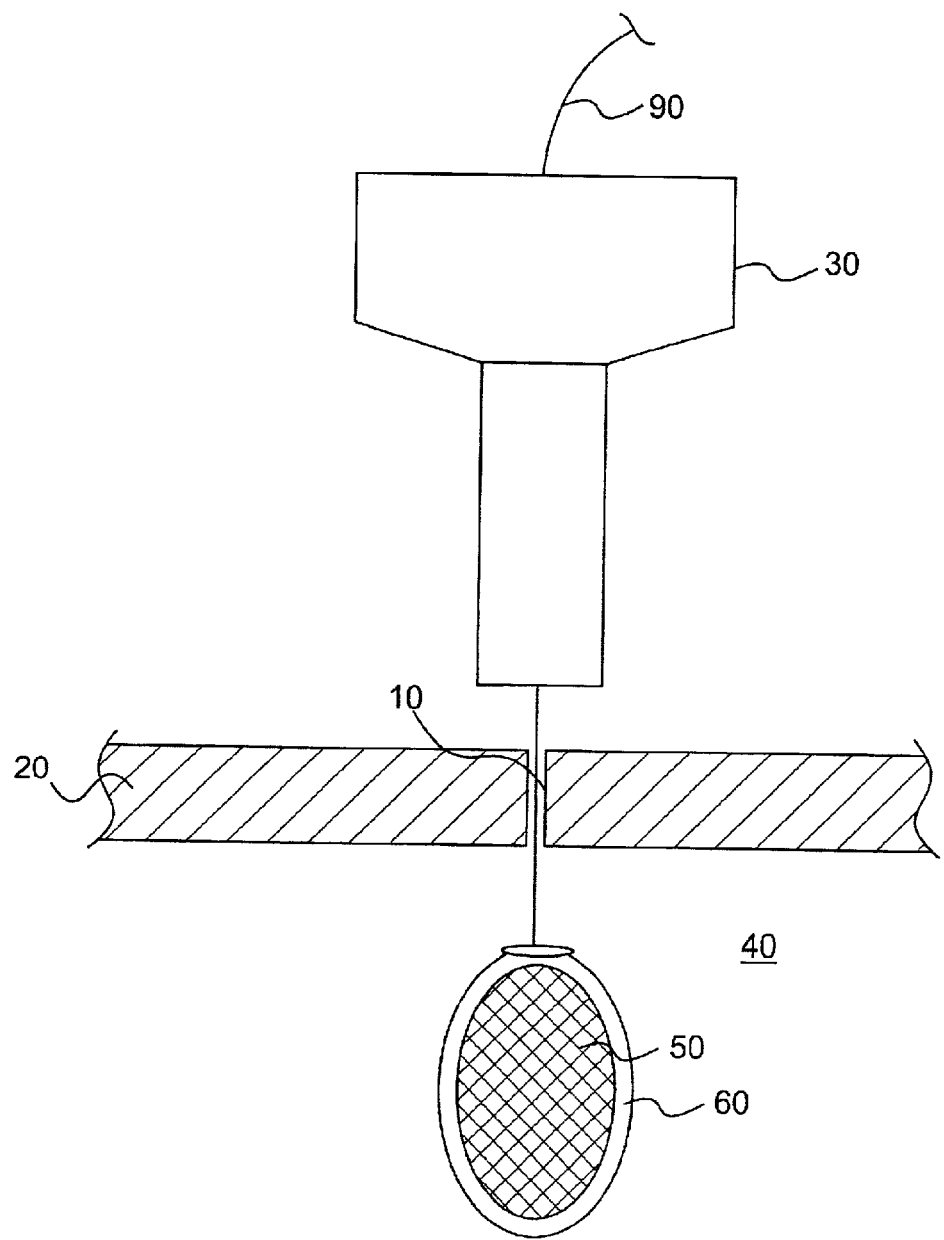
Figure 14:
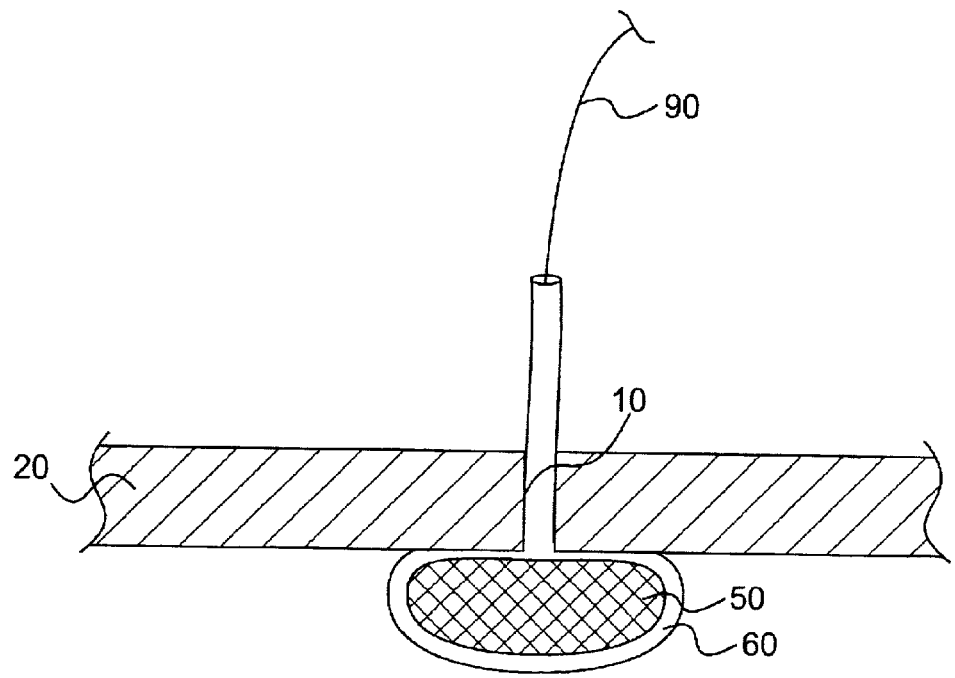

As illustrated in FIG. 10, the surgeon then simultaneously pulls on the purse string 410 and the port 120 in the direction of the arrow to extract the sheath 130, endo-bag 400, and specimen 50 through the incision 10. Because the abdominal wall 20 includes a tough, fibrous layer of fascia, the incision 10 resists expansion as the prongs 270, endo-bag 400, and specimen 50 are extracted. As a result, the prongs 270 contract radially-inwardly under the contracting force of the incision 10, which, in turn, causes the prongs 270, in combination with the elongated endo-bag 400, to manipulate the specimen 50 into an elongated, narrow shape that approximates the inside bore shape of the contracted sheath 130 and more easily squeezes through the incision 10. The smooth outer surfaces of the prongs 270 act like shoe horns for the specimen 50 and endo-bag 400 to further facilitate extraction of the specimen 50 through the incision 10. Consequently, the surgeon can extract the specimen 50 and endo-bag 400 from the abdominal cavity 40 through the incision 10 without having the specimen 50 bunch up in the endo-bag 400, as is disadvantageously the case with conventional extraction techniques.

The LSEP 100 of the present invention enables a surgeon to extract a specimen 50 using less force than conventional techniques and without having to enlarge the incision 10. The LSEP 100 advantageously prevents the specimen 50 from bunching in the endo-bag 400 and causing further complications during surgery. The LSEP 100 also minimizes the risk of rupturing the specimen 50 or endo-bag 400 and reduces the risk of spreading infectious, bilious, and/or cancerous material into the incision 10.

Various features of the LSEP 100 of the present invention have been exaggerated in the figures to more clearly illustrate their structure. For example, the diameter of the forward portion 160 has been exaggerated in order to clearly illustrate the outer surface 170 and how the forward portion 160 interacts with the prongs 270. The figures are provided for illustrative purposes only and do not illustrate the precise relative dimensions of the components of the LSEP 100.

The foregoing illustrated embodiments are provided to illustrate the structural and functional principles of the present invention and are not intended to be limiting. To the contrary, the principles of the present invention are intended to encompass any and all changes, alterations and/or substitutions within the spirit and scope of the following claims.

What is claimed is:

1. A laparoscopic specimen extraction port having expanded and contracted positions, the laparoscopic specimen extraction port comprising:

an elongated, hollow port having a rearward portion, an intermediate portion, and a forward portion that is radially-enlarged relative to the intermediate portion;

a holding ring disposed radially-outwardly from the intermediate portion and adapted to slide relative to the intermediate portion, the holding ring being disposed at a rear end of the intermediate portion when the laparoscopic specimen extraction port is in the contracted position; and a plurality of circumferentially-spaced prongs having rearward ends connected to the holding ring and forward ends extending to the radially-enlarged, forward portion, the forward ends of the prongs expanding radially-outwardly relative to the rearward ends when the laparoscopic specimen extraction port is in the expanded position, wherein, during transition from the contracted to the expanded position, the radially-enlarged forward portion expands the prongs radially-outwardly, and wherein each prong has an arced cross-section and is thinner than it is wide.

2. A laparoscopic specimen extraction port according to claim 1, wherein the forward portion is radially-enlarged relative to an inside surface of the holding ring such that the forward portion prevents the holding ring from sliding forwardly beyond the forward portion.

3. A laparoscopic specimen extraction port according to claim 1, further comprising a releasable holding mechanism to selectively secure the holding ring at the rear end of the intermediate portion when the laparoscopic specimen extraction port is in the contracted position.

4. A laparoscopic specimen extraction port according to claim 3, wherein rotation of the port relative to the holding ring disengages the holding mechanism to allow the laparoscopic specimen extraction port to be manipulated into the expanded position.

5. A laparoscopic specimen extraction port according to claim 4, wherein the holding mechanism comprises:

a forwardly-facing surface defined by the holding ring;

a notch on an inside surface of the holding ring, the notch extending rearwardly from the forwardly-facing surface; and a protrusion extending from the outer surface of the intermediate portion, a rearward edge of the protrusion being in front of the forwardly-facing surface when the laparoscopic specimen extraction port is in the contracted position to prevent the port from moving rearwardly relative to the holding ring, wherein rotation of the port relative to the holding ring aligns the protrusion with the notch, thereby allowing the protrusion to move through the notch and the port to move rearwardly relative to the holding ring to permit the laparoscopic specimen extraction port to be manipulated into the expanded position.

6. A laparoscopic specimen extraction port according to claim 2, wherein the forward portion of the port comprises a radially-outwardly-tapering outer surface.

7. A laparoscopic specimen extraction port according to claim 6, wherein each prong includes a forward tip that has inside and outside surfaces, and wherein the inside surface of the forward tip tapers radially-outwardly so that, when the laparoscopic specimen extraction port is in the contracted position, the outwardly-tapering inside surface of the forward tip of each prong adjoins the outwardly-tapering outer surface of the forward portion of the port.

8. A laparoscopic specimen extraction port according to claim 7, wherein the forward portion of the port includes a tip that tapers radially-inwardly from the forward portion.

9. A laparoscopic specimen extraction port according to claim 2, wherein the prongs comprise a flexible material that expands radially-outwardly during expansion of the laparoscopic specimen extraction port.

10. A laparoscopic specimen extraction port according to claim 1, wherein the prongs comprise at least one of plastic and PVC.

11. A laparoscopic specimen extraction port according to claim 2, wherein an indentation is formed on a surface of the holding ring to define a folding line between the holding ring and the prongs.

12. A laparoscopic specimen extraction port according to claim 2, wherein the rearward portion of the port is funnel-shaped and tapers radially inwardly toward the intermediate portion.

13. A laparoscopic specimen extraction port according to claim 1, wherein the prongs are tinted a color easily distinguishable from tissue.

14. A laparoscopic specimen extraction port according to claim 1, wherein the prongs are at least partially radio-opaque.

15. A laparoscopic specimen extraction port according to claim 1, wherein a cross-section of an outer surface of the intermediate and forward portions comprises at least one of a circular cross-section and an ovoid cross-section.

16. A laparoscopic specimen extraction port according to claim 1, wherein a cross-section of an inside surface of the holding ring comprises at least one of a circular cross-section and an ovoid cross-section.

17. A laparoscopic specimen extraction port according to claim 1, wherein the prongs extend forwardly from a forwardmost point of the hollow port when the laparoscopic specimen extraction port is in the expanded position.

18. A laparoscopic specimen extraction port according to claim 1, wherein the prongs form a funnel shape when the laparoscopic specimen extraction port is in the expanded position.

19. A laparoscopic specimen extraction port according to claim 18, wherein the funnel shape formed by the prongs defines an open central portion that is shaped to accommodate an endo-bag.

20. A laparoscopic specimen extraction port having expanded and contracted positions, the laparoscopic specimen extraction port comprising:

an elongated, hollow port having a rearward portion, an intermediate portion, and a forward portion that is radially-enlarged relative to the intermediate portion;

a holding ring disposed radially-outwardly from the intermediate portion and adapted to slide relative to the intermediate portion, the holding ring being disposed at a rear end of the intermediate portion when the laparoscopic specimen extraction port is in the contracted position; and a plurality of circumferentially-spaced prongs having rearward ends connected to the holding ring and forward ends extending to the radially-enlarged, forward portion, the forward ends of the prongs expanding radially-outwardly relative to the rearward ends when the laparoscopic specimen extraction port is in the expanded position, wherein, during transition from the contracted to the expanded position, the radially-enlarged forward portion expands the prongs radially-outwardly, wherein the prongs form a funnel shape when the laparoscopic specimen extraction port is in the expanded position, and wherein each of the prongs have smooth edges that are shaped so as to not cut into a patient during surgery.

* * * * *